United States Patent [19]

Remy

[11] 4,242,349

[45] Dec. 30, 1980

[54] OREXIGENIC USE OF PYRROLO[2,1-b][3]BENZAZEPINES

[75] Inventor: David C. Remy, North Wales, Pa.

[73] Assignee: Merck & Co., Inc., Rahway, N.J.

[21] Appl. No.: 80,813

[22] Filed: Oct. 1, 1979

[51] Int. Cl.³ .......................................... A61K 31/445
[52] U.S. Cl. ................................................... 424/267
[58] Field of Search ......................................... 424/267

[56] References Cited

U.S. PATENT DOCUMENTS

| | | | |
|---|---|---|---|
| 3,981,877 | 9/1976 | Prugh | 424/267 |
| 4,148,903 | 4/1979 | Atkinson et al. | 424/267 |
| 4,160,031 | 7/1979 | Remy | 424/267 |

*Primary Examiner*—Douglas W. Robinson
*Attorney, Agent, or Firm*—Mario A. Monaco; William H. Nicholson

[57] ABSTRACT

Pyrrolo[2,1-b][3]benzazepines with a piperidinylidene group in the 11-position have utility as appetite stimulants.

5 Claims, No Drawings

OREXIGENIC USE OF PYRROLO[2,1-b][3]BENZAZEPINES

BACKGROUND OF THE INVENTION

This invention is concerned with a novel method of stimulating appetite comprising the administration of an 1-methyl-4-[11H-pyrrolo[2,1-b][3]benzazepin-11-ylidene]piperidine, a 5,6-dihydro analog or derivatives thereof.

These compounds are known and known to have antipsychotic, antihistaminic, and antiserotonin activities as disclosed in U.S. Pat. No. 4,148,903.

Cyproheptadine and certain derivatives thereof, particularly 3-carboxycyproheptadine (U.S. Pat. No. 3,981,877) and 10,11-dihydro-3-carboxycyproheptadine (U.S. Pat. No. 4,160,031) are known to be appetite stimulants.

Also, 1-methyl-4-(9-carboxy-11H-pyrrolo[2,1-b][3]benzazepin-11-ylidene)piperidine is also an appetite stimulant as disclosed in U.S. Ser. No. 960,812, filed Nov. 15, 1978.

It is an object of this invention to provide a novel method of producing appetite stimulation by the administration of certain of the known pyrrolo[2,1-b][3]benzazepines.

DETAILED DESCRIPTION OF THE INVENTION

The compounds active in the method of the present invention have the following structural formula:

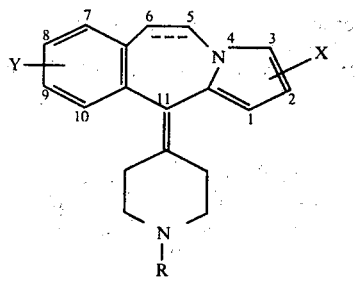

or pharmaceutically acceptable salt thereof, wherein the dotted line represents saturation or unsaturation; X and Y are independently
(1) hydrogen,
(2) halogen such as chloro, bromo, fluoro, or iodo,
(3) trifluromethyl,
(4) lower alkyl, especially $C_{1-4}$ alkyl, or
(5) lower alkoxy, especially $C_{1-4}$ alkoxy,
and R is lower alkyl, especially $C_{1-4}$ alkyl.

A preferred embodiment of the novel compounds of this invention is the compound of structural formula:

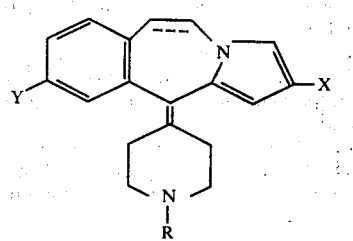

or pharmaceutically acceptable salt thereof, wherein X, Y, and R are as defined above.

A still more preferred embodiment is where one of X and Y is hydrogen, and the other is hydrogen, halo, trifluoromethyl or lower alkyl.

Also active in the novel method of the present invention are pharmaceutically acceptable acid addition salts. These salts, prepared by conventional means, include the hydrochloride, maleate, sulfate, phosphate, citrate, tartrate, succinate, and the like.

In the method of treatment of the present invention it is noted that the precise unit dosage form and dosage level depend upon the case history of the individual being treated and consequently are left to the discretion of the therapist. In general, however, the compounds described above produce the desired effect of appetite stimulation when given at from about 0.01 to about 10.0 mg per kg body weight per day. The preferred form of delivery of the instant compounds for appetite stimulation of domestic animals is by solution in drinking water or preformulated feedstuffs. For human and animal administration, any of the usual pharmaceutical oral forms may be employed such as tablets, elixirs and aqueous suspensions comprising from about 0.01 to about 10.0 mg of the compounds of this invention per kg body weight given daily. Thus, for example, tablets given 2-4 times per day comprising from about 0.5 to about 50 mg of the compounds of this invention are suitable for human treatment. Sterile solutions (representatively given for human treatment) for injection comprising from about 0.1 to about 10.0 mg of the compounds of this invention given two to four times daily are also suitable means of delivery.

EXAMPLE

Appetite Stimulant Studies in Cats

METHODS

Adult male cats, individually caged with water available ad libitum, are allowed to eat for only three hours daily (at the same time each day). The animals are maintained on this feeding schedule for at least four weeks prior to testing. A preweighed test meal (C/D Feline, Dietary Animal Food, Riviana Foods, Inc.) is presented to each cat, and after 30 minutes, 60 minutes and three hours, the amount consumed is determined by reweighing the remaining food. An amount of food is presented insuring a surplus, thus allowing unrestricted intake. Food eaten on the test (drug) day is compared with the amount consumed on the immediately preceding (control) day. Test compounds suspended in 1% methylcellulose are administered by gavage 30 minutes preceding presentation of the test meal. No cat is given a test compound more often than once weekly.

Cyproheptadine and two related compounds are compared in a crossover study employing the methods described above. Cyproheptadine and the test compounds are given at two dose levels (0.25 and 0.5 mg/kg p.o.), using a separate group of ten cats for each dose. All doses refer to the free base. Five cats in each group of ten receive a particular dose of cyproheptadine first and the remaining five cats receive the same dose of a test compound (on the same day). The following week, those animals that previously received cyproheptadine are given the test compound and vice versa. The percent increase in food intake on the test day is determined for each cat. The percent values obtained from cyproheptadine and the test compound are compared in a nonpaired t-test.

RESULTS

The data are summarized in Tables 1, 2 and 3. L-634,935, and L-641,867 significantly increased food intake in cats at both dose levels and at all three test times.

TABLE 1
CROSSOVER COMPARISON OF CYPROHEPTADINE WITH RELATED COMPOUNDS

| Compound | Dose mg/kg p.o. | Average Grams Consumed[a] Preceding Day/Test Day | | |
|---|---|---|---|---|
| | | 30 min | 60 min | 180 min |
| Cyproheptadine | 0.25 | 91 ± 38/175 ± 29* | 124 ± 39/212 ± 42* | 175 ± 50/239 ± 41* |
| | 0.5 | 109 ± 38/193 ± 63* | 131 ± 39/220 ± 53* | 170 ± 46/236 ± 50* |
| L-634,935-01B-01 | 0.25 | 95 ± 33/182 ± 24* | 132 ± 35/203 ± 35* | 170 ± 42/229 ± 47* |
| | 0.5 | 117 ± 39/204 ± 60* | 137 ± 35/219 ± 55* | 166 ± 32/234 ± 49* |
| Cyproheptadine | 0.25 | 109 ± 34/165* ± 34 | 129 ± 35/200* ± 41 | 179 ± 45/231* ± 52 |
| | 0.5 | 135 ± 47/190* ± 63 | 157 ± 50/221* ± 50 | 194 ± 50/256* ± 35 |
| L-641,867-01S-01 | 0.25 | 113 ± 33/172* ± 20 | 134 ± 40/208* ± 37 | 183 ± 46/239* ± 37 |
| | 0.5 | 133 ± 51/189* ± 49 | 148 ± 44/217* ± 41 | 193 ± 46/243* ± 33 |

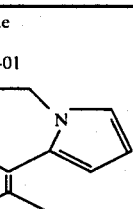

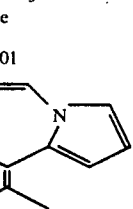

*Significant increase (P <0.05, 2-tailed paired t-test; test day vs. control day)
[a]N = 10

TABLE 2
DATA EXPRESSED AS % INCREASE IN FOOD CONSUMPTION

| Treatment | Dose mg/kg p.o. | % Increase in Food Consumption (X ± SD)[a] | | |
|---|---|---|---|---|
| | | 30 min | 60 min | 180 min |
| Cyproheptadine (L-574,452-01P) | 0.25 | 114.4±63.3 | 80.1±42.9 | 42.8±27.4 |
| | 0.5 | 89.6±59.2 | 74.8±38.2 | 42.4±25.2 |
| L-634,935-01B-01 | 0.25 | 114.6±76.6 | 59.5±31.3 | 37.4±15.7 |
| | 0.5 | 77.8±27.3 | 60.6±20.8 | 41.6±22.1 |
| Cyproheptadine (L-574,452-01P) | 0.25 | 57.3±38.4 | 58.7±27.5 | 31±17.6 |
| | 0.5 | 50±54.7 | 52.4±52.3 | 41.5±48.0 |
| L-641,867-01S-01 | 0.25 | 63.3±50.0 | 62.7±39.9 | 35.5±25.1 |
| | 0.5 | 51.6±48.4 | 52±33.8 | 30.6±24.1 |

[a]N = 10

TABLE 3
QUANTAL REPRESENTATION OF THE RESULTS

| Treatment | Dose mg/kg p.o. | # Cats with 20% or greater increase in food intake[a] minutes[b] | | |
|---|---|---|---|---|
| | | 30 | 60 | 180 |
| Cyproheptadine | 0.25 | 9 | 9 | 8 |
| | 0.5 | 10 | 10 | 9 |
| L-634,935 | 0.25 | 10 | 9 | 9 |
| | 0.5 | 10 | 10 | 9 |
| Cyproheptadine | 0.25 | 9 | 10 | 8 |
| | 0.5 | 6 | 8 | 7 |
| L-641,867 | 0.25 | 9 | 10 | 8 |
| | 0.5 | 8 | 9 | 6 |

[a]Test day vs. control day; N = 10
[b]Minutes post feeding

What is claimed is:

1. A method of stimulating appetite comprising administering to a patient in need of such treatment an effective appetite stimulating amount of a compound of structural formula:

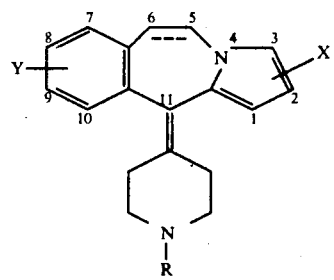

or a pharmaceutically acceptable salt thereof, wherein the dotted line represents saturation or unsaturation; X and Y are independently hydrogen halogen, lower alkyl, or lower alkoxy; and R is lower alkyl.

2. The method of claim 1 wherein X and Y are on the 2 and 9 positions respectively.

3. The method of claims 1 or 2 wherein one of X and Y is hydrogen, and the other is hydrogen, halo, trifluoromethyl or lower alkyl.

4. The method of claim 1 wherein the compound is 1-Methyl-4-[6,11-dihydro-5H-pyrrolo[2,1-b][3]benzazepin-11-ylidene]piperidine or a non-toxic pharmaceutically acceptable salt thereof.

5. The method of claim 1 wherein the compound is 1-Methyl-4-[11H-pyrrolo[2,1-b][3]benzazepin-11-ylidene]piperidine or a non-toxic pharmaceutically acceptable salt thereof.

* * * * *